(12) United States Patent
Liu et al.

(10) Patent No.: US 7,324,628 B2
(45) Date of Patent: Jan. 29, 2008

(54) METHOD OF TESTING A MEDICAL IMAGING DEVICE

(75) Inventors: James Zhengshe Liu, Glenview, IL (US); Olgun Kukrer, Waukesha, WI (US); Kenneth Scott Kump, Waukesha, WI (US); Jon C. Omernick, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 251 days.

(21) Appl. No.: 11/197,029

(22) Filed: Aug. 4, 2005

(65) Prior Publication Data
US 2006/0239415 A1   Oct. 26, 2006

Related U.S. Application Data

(60) Provisional application No. 60/673,897, filed on Apr. 22, 2005.

(51) Int. Cl.
*H05G 1/54* (2006.01)
*G01N 23/04* (2006.01)
(52) U.S. Cl. .................. 378/117; 378/98.8; 378/207
(58) Field of Classification Search .............. 378/98.8, 378/117, 207
See application file for complete search history.

(56) References Cited

U.S. PATENT DOCUMENTS

| 5,604,781 | A  | * | 2/1997  | Suzuki et al. .................. 378/62 |
| 6,333,963 | B1 | * | 12/2001 | Kaifu et al. ................ 378/98.2 |
| 6,457,861 | B1 | * | 10/2002 | Petrick et al. ............... 378/207 |
| 6,461,040 | B1 | * | 10/2002 | Mattson et al. .............. 378/205 |
| 6,744,848 | B2 | * | 6/2004  | Stanton et al. ................. 378/55 |
| 6,928,145 | B2 | * | 8/2005  | Kobayashi ................... 378/117 |
| 7,026,608 | B2 | * | 4/2006  | Hirai ....................... 250/252.1 |
| 7,030,387 | B2 | * | 4/2006  | Serebryanov et al. .. 250/370.15 |
| 7,172,340 | B2 | * | 2/2007  | Oota .......................... 378/189 |
| 7,187,754 | B2 | * | 3/2007  | Hahm et al. ................ 378/98.7 |
| 2005/0100128 | A1 | * | 5/2005 | Hilderscheid et al. ........ 378/19 |
| 2005/0161610 | A1 | * | 7/2005 | Spahn .................... 250/370.09 |

\* cited by examiner

*Primary Examiner*—Edward J. Glick
*Assistant Examiner*—Thomas R. Artman
(74) *Attorney, Agent, or Firm*—McAndrews, Held & Malloy, Ltd.; Peter J. Vogel; Michael A. Dellapenna

(57) ABSTRACT

A method of testing a portable x-ray device includes sensing an environmental stimulus experienced by the portable x-ray device, transmitting a signal related to the environmental stimulus to a processing unit, determining whether the signal meets an alert threshold, activating a detector of the portable x-ray device if the signal meets the alert threshold, producing a gray image through the activating step, comparing the gray image produced through the activating step with a control gray image corresponding to a properly functioning detector.

19 Claims, 3 Drawing Sheets

METHOD OF TESTING A MEDICAL IMAGING DEVICE

RELATED APPLICATIONS

This application relates to and claims priority benefits from U.S. Provisional Patent Application No. 60/673,897 entitled "Method Of Testing A Medical Imaging Device," filed Apr. 22, 2005, which is incorporated by reference herein in its entirety.

BACKGROUND OF THE INVENTION

Embodiments of the present invention provide a method of assuring proper operation of a medical imaging device, and, more particularly, to a method of testing a portable x-ray device to determine if it is operating properly.

Portable x-ray systems are used to image anatomical structures within various settings. For example, a technician may use a portable x-ray system to image an object of interest, such as a forearm, in a hospital bedroom setting. The technician may image the object with the x-ray system, and then leave the room with the portable system to image another patient in another location. The imaging system is susceptible to damage because it is portable and easily moved to different locations. For example, the system may be tipped over, dropped and/or struck, thereby causing damage to the detector or other components.

In order to determine whether the imaging system is functioning properly, an operator typically runs a test imaging process in which x-rays are emitted from the source and received by the detector. The resulting image usually provides enough information for the operator to determine if the system is operating properly. For example, if the resulting image contains various types of distortion, the operator determines that the system has been damaged and needs repair.

Testing the system through a full imaging process, however, takes time, and exposes the environment to x-rays. Thus, a need exists for an efficient, safe, and quick method of testing an imaging system, such as a portable x-ray system.

SUMMARY OF THE INVENTION

Certain embodiments of the present invention provide a method of testing a portable x-ray device that includes sensing an environmental stimulus experienced by the portable x-ray device, transmitting a signal related to the environmental stimulus to a processing unit, determining whether the signal meets an alert threshold, activating a detector of the portable x-ray device if the signal meets the alert threshold, producing a gray image through the activating step, comparing the gray image produced through the activating step with a control gray image corresponding to a properly functioning detector. The environmental stimulus may be a physical shock to the portable x-ray device measured by a sensor, such as an accelerometer. The environmental stimulus may also be a power surge, temperature of the portable x-ray device, or an ambient temperature, each of which are measured by an appropriate sensor.

Certain embodiments of the present invention also provide a system for testing imaging quality of a portable x-ray device including a portable x-ray device having an x-ray source, a detector, and at least one sensor adapted to sense at least one environmental stimulus, and a processing unit in communication with the sensor. The processing unit receives a stimulus signal from the sensor and determines whether the stimulus signal meets a predetermined alert threshold related to damage to said portable x-ray device. The processing unit activates the detector if the stimulus signal meets the predetermined alert threshold to produce a gray image. The processing unit then compares the gray image with a control gray image corresponding to a properly functioning detector. The system may also include a monitor in communication with the processing unit, wherein the processing unit is responsive to display an alert message on the monitor if the stimulus signal meets the predetermined threshold.

Figure 1:
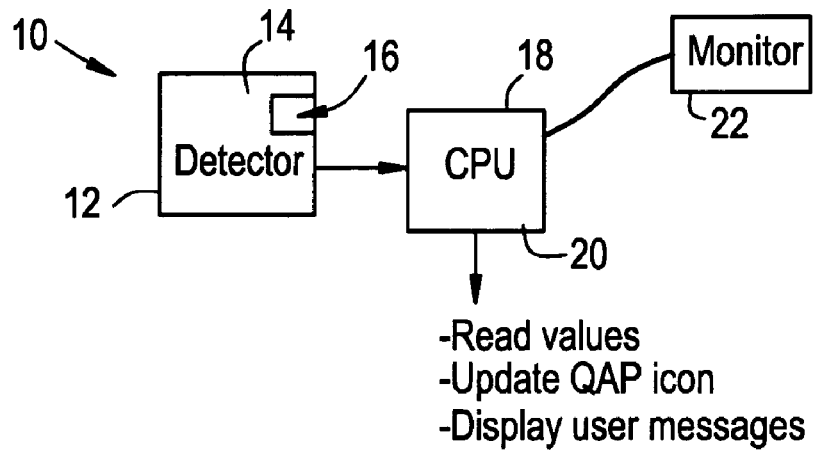
FIG. 1 illustrates a simplified block diagram of a portable x-ray imaging system, according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates a simplified block diagram of a portable x-ray imaging system 10, according to an embodiment of the present invention. The x-ray system 10 includes a portable x-ray device 12 including a detector 14 having a sensor 16 mounted or otherwise secured thereto. The detector 14 and the sensor 16 are in communication with a computer 18 having a central processing unit (CPU) 20, which is also in communication with a monitor 22. The components of the system 10 may be in communication with each other through wired or wireless connections.

The sensor 16 may be any type of sensing device that is configured to detect movement. For example, the sensor 16 may be an accelerometer. If the x-ray device 12 is tipped over, dropped or struck, the sensor 16 measures the physical shock, jolt, etc. absorbed by the x-ray device 12. The CPU 20 then receives a signal from the sensor 16 related to the measured shock. The CPU 20 is programmed to determine whether a threshold alert shock level, which is a minimum level at which damage to the system 10 may occur, has been met. That is, the CPU 20 compares the sensed shock to a stored threshold alert shock level. Once the threshold alert shock level is reached, the CPU 20 displays an alert indicator on the monitor 22.

Alternatively, the sensor 16 may be, or also include, a temperature sensing device, such as a thermometer. The CPU 20 receives signals from the thermometer, and is configured to determine a threshold alert temperature level, at (or below or above) which, the system 10 may be damaged. That is, the imaging capabilities of the system 10 may degrade or be damaged if the system 10 is too hot or cold, of if the environment in which the system 10 is located is too hot or too cold. The CPU 20 compares the sensed temperature with a stored threshold alert temperature level. Once the threshold alert temperature level is reached, the CPU 20 displays an alert indicator on the monitor 22.

Figure 2:
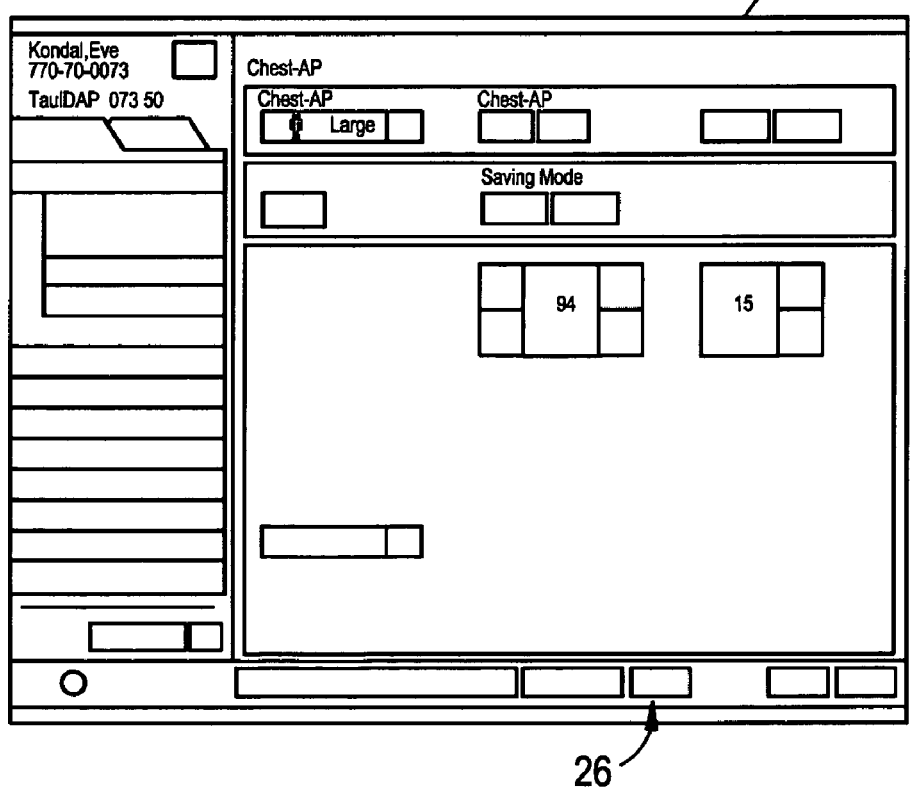
FIG. 2 illustrates an exemplary screen shot of an imaging application, according to an embodiment of the present invention.

FIG. 2 illustrates an exemplary screen shot 24 of an imaging application, according to an embodiment of the present invention. An alert may appear on the monitor 20 indicating a threshold alert shock level, or temperature level. An operator may then click on, or touch (if the monitor is a touchscreen), a "QAP" (quality assurance procedure) button located on the screen 24. The CPU 20 then performs an imaging test procedure.

Figure 3:
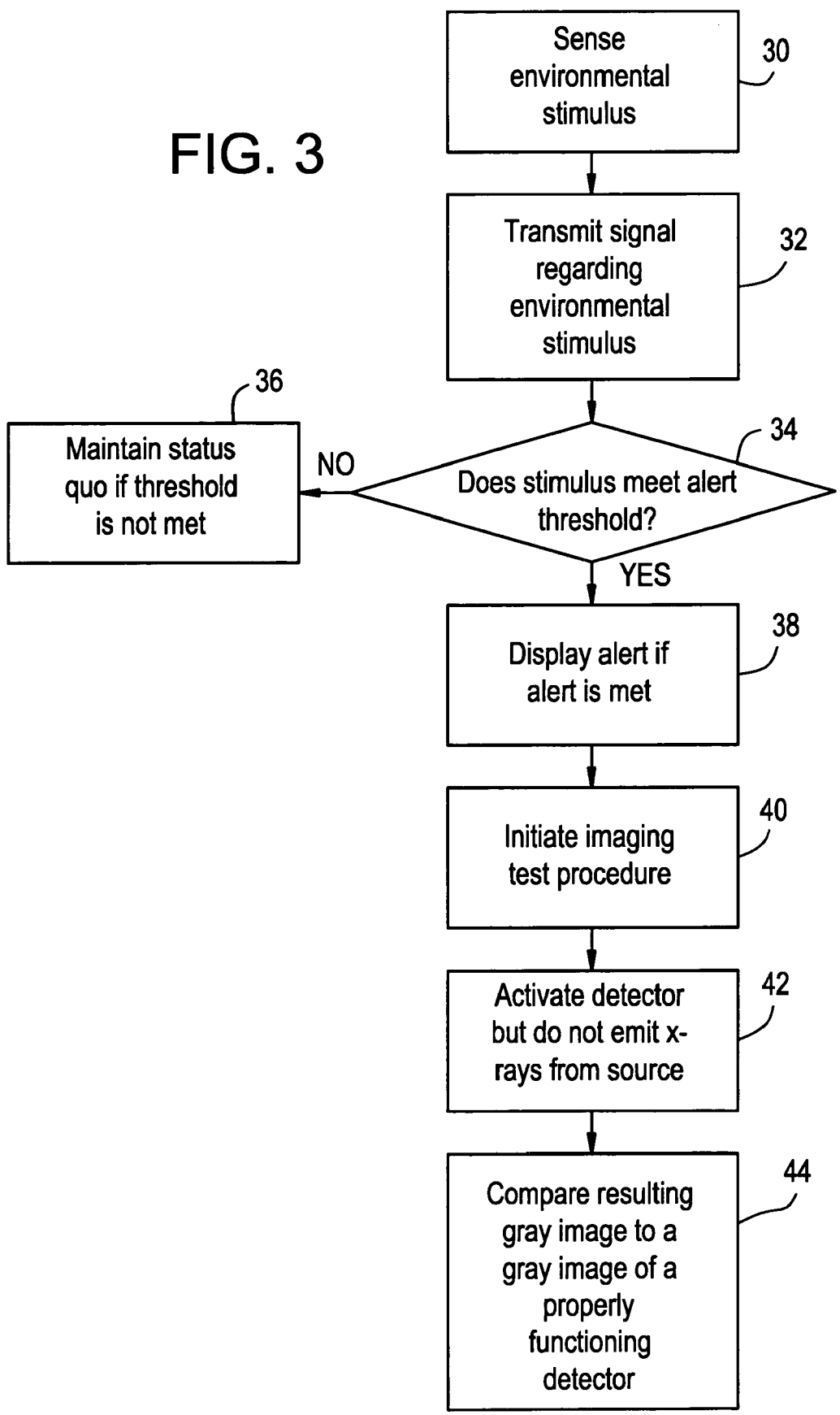
FIG. 3 illustrates a flow chart of an imaging test procedure, according to an embodiment of the present invention.

FIG. 3 illustrates a flow chart of an imaging test procedure, according to an embodiment of the present invention. Referring to FIGS. 1-3, at 30, the sensor 16 senses an environmental stimulus, such as a physical shock (e.g., the x-ray device 12 is dropped, bumped or struck) or a temperature. At 32, the sensor 16 sends a signal regarding the environmental stimulus to the CPU 20. The CPU 20 determines whether the sensed environmental stimulus meets an alert threshold at 34. If the sensed environmental stimulus does not meet the alert threshold, the CPU 20 maintains a status quo, in which it does not issue an alert at 36. If, however, the sensed environmental stimulus does meet the alert threshold, the CPU 20 operates to display an alert message on the monitor 22 at 38, in which the CPU 20 suggests an imaging test. At 40, a user then may initiate a test procedure by clicking on, or touching, a "QAP" icon or button displayed on the monitor 22.

The imaging test does not emit x-rays during the imaging procedure. Instead, the imaging test performs an imaging process in which x-rays are not emitted, but the detector 14 is activated at 42. Activation of the detector, but not the x-ray source, produces a dark image. A user and/or the processing unit 20 may determine whether the detector 14 has been damaged through the resulting gray screen at 44. For example, a properly functioning detector produces a known proper dark image. If the resulting dark image matches the proper dark image, the user and/or the CPU 20 determines that the detector 14 has not been damaged. However, if the resulting dark image deviates from the proper dark image, the user and/or the CPU 20 determines that the detector 14 has been damaged. As such, a quick and safe imaging test procedure is performed without emitting x-rays, or performing a full imaging process. In general, embodiments of the present invention provide an efficient, safe, and quick method of testing an imaging system, such as a portable x-ray system.

Figure 4:
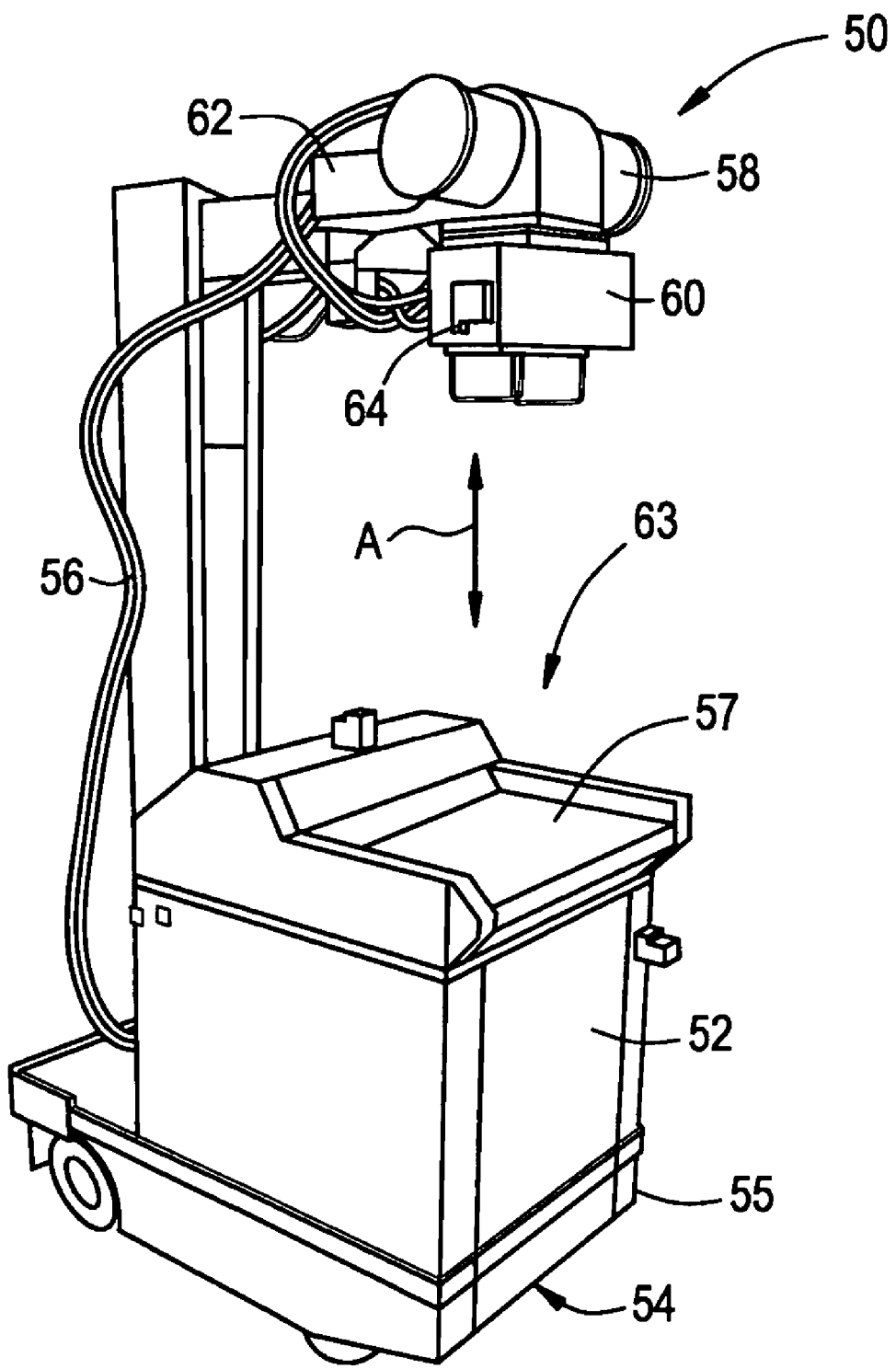
FIG. 4 illustrates an isometric view of a portable x-ray imaging device, according to an embodiment of the present invention.

FIG. 4 illustrates an isometric view of a portable x-ray imaging device 50, according to an embodiment of the present invention. The x-ray imaging device 50 includes a main body 52 supported by a wheeled support structure 54. The main body 52 includes a base 55 having a detector 57. An upright support 56 extends from the wheeled support structure 54 and/or the base 55 and supports a source assembly 58. The source assembly 58 includes an x-ray source 60 connected to a support 62 that is movably connected to the upright support 56. As such, the x-ray source 60 may be moved relative to the detector 57 over directions indicated by arrow A. An object to be imaged is positioned within an imaging area 63, located between the x-ray detector 57 and the x-ray source 60.

A sensor(s) 64, as discussed above, is mounted on the x-ray source 60. Alternatively, the sensor(s) 64 may be mounted to the detector 57, the upright support 56, and/or various other components of the portable x-ray imaging device 50. The sensor(s) 64 is configured to detect environmental stimuli, such as physical shocks, temperature, ambient temperature or pressure, electrical or electromagnetic phenomena, or various other such stimuli. A computer (not shown in FIG. 4) is in communication with the sensor(s) 64 and is responsive to determine whether sensed environmental stimuli meet an alert threshold, as discussed above with respect to FIG. 3.

Various embodiments of the present invention provide a method and system of testing a medical imaging device. The medical imaging device may be a portable fluoroscopic imaging device such as an X-ray C-arm system, an ultrasound imaging system, a single photon emission computed tomography (SPECT) system, a computed tomography (CT) system, an optical coherence tomography (OCT) system, a positron emission tomography (PET) imaging system, and the like.

For example, embodiments of the present invention may be used with an X-ray C-arm having an X-ray source positioned on one distal end of the arm, with a detector positioned on the other distal end of the arm, such as shown and described in U.S. Pat. No. 6,104,780, entitled "Mobile bi-planar fluoroscopic imaging apparatus," U.S. Pat. No. 5,802,719, entitled "One piece C-arm for X-ray diagnostic equipment," and U.S. Pat. No. 5,627,873, entitled "Mini C-arm assembly for mobile X-ray imaging system," all of which are hereby incorporated by reference in their entireties. Optionally, the imaging system may be an MR system, such as described in U.S. Pat. No. 6,462,544, entitled "Magnetic resonance imaging apparatus," which is also hereby incorporated by reference in its entirety.

Additionally, embodiments of the present invention may also be used with Positron Emission Tomography (PET), such as shown and described in U.S. Pat. No. 6,337,481, entitled "Data binning method and apparatus for PET tomography including remote services over a network," which is hereby incorporated by reference in its entirety, Single Photon Emission Computed Tomography (SPECT), such as shown and described in U.S. Pat. No. 6,194,725, entitled "SPECT system with reduced radius detectors," which is hereby incorporated by reference in its entirety, Electron Beam Tomography (EBT), such as shown and described in U.S. Pat. No. 5,442,673, entitled "Fixed septum collimator for electron beam tomography," which is hereby incorporated by reference in its entirety, and various other imaging systems.

Embodiments of the present invention may also be used with navigation and tracking systems as those described in U.S. Pat. No. 5,803,089, entitled "Position Tracking and Imaging System for Use in Medical Applications," which is hereby incorporated by reference in its entirety.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

The invention claimed is:

1. A method of testing imaging quality of a medical imaging device, comprising:

sensing an environmental stimulus experienced by the medical imaging device;

transmitting a signal related to the environmental stimulus to a processing unit;

determining whether the signal meets an alert threshold;

activating only a detector of the medical imaging device if the signal meets the alert threshold;

producing a gray image through said activating; and comparing the gray image produced through said activating with a control gray image corresponding to a properly functioning detector in order to determine the imaging quality of the medical imaging device.

2. The method of claim 1, wherein the medical imaging device is a portable x-ray device.

3. The method of claim 1, wherein the environmental stimulus is a physical shock to the medical imaging device.

4. The method of claim 1, wherein the environmental stimulus is a power surge.

5. The method of claim 1, wherein the environmental stimulus is a temperature of the medical imaging device.

6. The method of claim 1, wherein the environmental stimulus is an ambient temperature.

7. The method of claim 1, further comprises providing a sensor on or within the medical imaging device, wherein said sensing comprises sensing an environmental stimulus through said sensor.

8. The method of claim 7, wherein the sensor comprises an accelerometer.

9. The method of claim 7, wherein the sensor comprises a thermometer.

10. The method of claim 1, further comprising displaying an alert graphic if the signal meets the alert threshold.

11. A system for testing imaging quality of a portable x-ray device, comprising:

a portable x-ray device comprising (i) an x-ray source; (ii) a detector; and (iii) at least one sensor adapted to sense at least one environmental stimulus; and a processing unit in communication with said at least one sensor, said processing unit receiving a stimulus signal from said at least one sensor, said processing unit responsive to determine whether the stimulus signal meets a predetermined alert threshold related to damage to said portable x-ray device in order to test the imaging quality of the portable x-ray device, wherein said processing unit is responsive to activate only said detector if the stimulus signal meets the predetermined alert threshold to produce a gray image, and wherein said processing unit compares the gray image with a control gray image corresponding to a properly functioning detector.

12. The system of claim 11, further comprising a monitor in communication with said processing unit, wherein said processing unit is responsive to display an alert message on said monitor if the stimulus signal meets the predetermined threshold.

13. The system of claim 11, wherein the environmental stimulus is a physical shock to the portable x-ray device.

14. The system of claim 11, wherein the environmental stimulus is a power surge.

15. The system of claim 11, wherein the environmental stimulus is a temperature of the portable x-ray device.

16. The system of claim 11, wherein the environmental stimulus is an ambient temperature.

17. The system of claim 11, wherein said at least one sensor comprises an accelerometer.

18. The system of claim 11, wherein said at least one sensor comprises a thermometer.

19. A method of testing imaging quality of an x-ray imaging device, comprising:

providing at least one stimulus sensor on or within the x-ray imaging device;

sensing an environmental stimulus experienced by the x-ray imaging device through the at least one stimulus sensor, wherein the environmental stimulus includes at least one of a physical shock, power surge, temperature of the x-ray imaging device, and ambient temperature of an imaging environment;

transmitting a signal related to the environmental stimulus to a processing unit;

determining whether the signal meets an alert threshold;

displaying an alert graphic if the signal meets the alert threshold;

activating only a detector of the x-ray imaging device if the signal meets the alert threshold;

producing a gray image through said activating; and comparing the gray image produced through said activating with a control gray image corresponding to a properly functioning detector in order to determine the imaging quality of the x-ray imaging device.

* * * * *